US008757035B2

(12) United States Patent
Kerboul et al.

(10) Patent No.: US 8,757,035 B2
(45) Date of Patent: Jun. 24, 2014

(54) TORQUE LIMITING RATCHET DEVICE

(75) Inventors: Guillaume Kerboul, Quimper (FR);
Stuart G. Weekes, Oxford (GB); James William Truscott, Swindon (GB)

(73) Assignee: Symmetry Medical, Inc., Bedford, MA (US)

(*) Notice: Subject to any disclaimer, the term of this patent is extended or adjusted under 35 U.S.C. 154(b) by 266 days.

(21) Appl. No.: 13/331,524

(22) Filed: Dec. 20, 2011

(65) Prior Publication Data

US 2013/0152746 A1 Jun. 20, 2013

(51) Int. Cl.
*B25B 23/142* (2006.01)
*B25B 13/46* (2006.01)
*A61B 17/88* (2006.01)
*A61B 19/00* (2006.01)

(52) U.S. Cl.
CPC ........... *B25B 23/1427* (2013.01); *B25B 13/466* (2013.01); *A61B 17/8875* (2013.01); *A61B 2019/301* (2013.01)
USPC .............................................. 81/475; 81/473

(58) Field of Classification Search
USPC .................................................... 81/473–476
See application file for complete search history.

(56) References Cited

U.S. PATENT DOCUMENTS 2,174,342 A * 9/1939 Greulich ......................... 464/39
5,576,501 A * 11/1996 Huang ....................... 73/862.23

* cited by examiner

*Primary Examiner* — David B Thomas
(74) *Attorney, Agent, or Firm* — Christopher & Weisberg, P.A.

(57) ABSTRACT

A ratchet tool, including a shaft defining a longitudinal axis; a handle coaxial to the shaft; a first gear immovably fixed to the shaft and disposed in the handle; a second gear rotatably and longitudinally movable with respect to the shaft, where the second gear engages the first gear to limit torque transfer from the handle to the shaft in a first direction and provides substantially zero torque transfer in a second direction; a first spring disposed between the second gear and the handle; a third gear rotatably and longitudinally movable with respect to the shaft, where the third gear engages the first gear to limit torque transfer from the handle to the shaft in the second direction and provides substantially zero torque transfer in the first direction; and a second spring disposed between the third gear and the handle.

20 Claims, 9 Drawing Sheets

TORQUE LIMITING RATCHET DEVICE

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to medical tools or devices for rotating or driving fasteners or hardware, and particularly, to adjusting or limiting the amount of torque applied to surgical fasteners or hardware.

BACKGROUND OF THE INVENTION

When inserting, tightening, or securing fasteners or hardware, it is desirous to control the precise amount of torque being delivered in many situations. This is of particular concern in surgical and medical procedures where application of excessive force can damage or destroy the hardware, or injure the patient. Such injury could have catastrophic consequences, especially when working with spinal and skeletal structures and related devices. Accordingly, drivers have been developed to limit the amount of torque delivered to the driven object or device.

However, improperly calibrated or tensioned devices can also do damage if too much torque is delivered or, conversely, will be ineffective if the tension in the device is too low. Moreover, difficulties and inaccuracies are multiplied when working parts of a tool become worn, or do not provide a consistent transferable torque after several uses. Accordingly, it is desirable to provide a torque-limiting driver operable to consistently and accurately deliver a maximum selected torque amount.

SUMMARY OF THE INVENTION

The present invention advantageously provides medical tools or devices for rotating or driving fasteners or hardware while adjusting or limiting the amount of torque applied to surgical fasteners or hardware. In particular, a tool having limited torque transference is disclosed, including a shaft; a first gear fixed to the shaft; a first tooth engageable with the first gear and rotatable with respect to the shaft; and a second tooth engageable with the first gear and rotatable with respect to the shaft, where a maximum torque threshold applied to the shaft in a first rotational direction is limited at least in part by a slope of the first tooth and a maximum torque threshold applied to the shaft in a second rotational direction is limited at least in part by a slope of the second tooth. At least one of the first or second teeth may be longitudinally movable with respect to the shaft. The tool may include a spring that resists the longitudinal movement of the at least one of the first or second teeth, and the resistance of the spring may be selectively adjustable. The tool may include a housing, wherein the shaft, first gear, first tooth, and second tooth are contained within the housing. The housing may be selectively engageable to the first tooth, the second tooth and/or the first gear.

A ratchet tool is provided, including a housing; a shaft passing through at least a portion of the housing and defining a longitudinal axis; a first gear immovably fixed to the shaft; a second gear disposed in the housing and rotatable with respect to the shaft; and a third gear disposed in the housing and rotatable with respect to the shaft, where a maximum torque transferable from the housing to the shaft in a first rotational direction is limited at least in part by the second gear and a maximum torque transferable from the housing to the shaft in a second rotational direction is limited at least in part by the third gear. The second and third gears may be coaxial with the shaft. The housing may be selectively engageable with the first gear, second gear, or third gear. The tool may include a selector pin movably coupled to the housing, where the selector pin is positionable in a plurality of positions to selectively engage the housing with the first gear, second gear, and/or third gear. The first gear, second gear, and third gear may each define a plurality of longitudinal splines, and the selector pin may be positional between two of the plurality of splines. The tool may include a sleeve coupled to the selector pin, the sleeve defining a plurality of rails engageable with a plurality of longitudinal splines defined by the second gear or third gear. The tool may include a first spring disposed between the second gear and the housing, and a second spring disposed between the third gear and the housing, where a compression of at least one of the first or second springs is selectively adjustable. The tool may include a cap coupled to the housing, where the cap is operable to adjust the compression of the first or second springs. The second gear may define at least one tooth engageable with the first gear, the tooth defining a first surface defining a first angle with respect to the longitudinal axis and a second surface defining a second angle with respect to the longitudinal axis, where the first angle is smaller than the second angle. The third gear may define at least one tooth engageable with the first gear, the tooth defining a first surface defining a first angle with respect to the longitudinal axis and a second surface defining a second angle with respect to the longitudinal axis, where the first angle is smaller than the second angle.

A ratchet tool is provided, including a shaft defining a longitudinal axis; a handle coaxial to the shaft; a first gear immovably fixed to the shaft and disposed in the handle; a second gear rotatably and longitudinally movable with respect to the shaft, wherein the second gear engages the first gear to limit torque transfer from the handle to the shaft in a first direction and provides substantially zero torque transfer in a second direction; a first spring disposed between the second gear and the handle; a third gear rotatably and longitudinally movable with respect to the shaft, wherein the third gear engages the first gear to limit torque transfer from the handle to the shaft in the second direction and provides substantially zero torque transfer in the first direction; and a second spring disposed between the third gear and the handle. The tool may include a cap coupled to the handle, where the cap is operable to adjust a compression of at least one of the first or second springs. The tool may include a selector element movably coupled to the handle to selectively engage the handle to one of the first gear, second gear, or third gear.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

The present invention advantageously provides medical tools or devices for rotating or driving fasteners or hardware while adjusting or limiting the amount of torque applied to surgical fasteners or hardware. Now referring to the figures in which like reference designators refer to like elements, there is shown in FIGS. 1-3 and 8-10 examples of a medical tool or instrument constructed in accordance with the principles of the present invention, designated generally as "10." The tool 10 may include a rotatable driver and/or ratchet tool 10 operable to turn a fastener or other hardware with a limited and/or selectable amount of applied torque.

Figure 1:
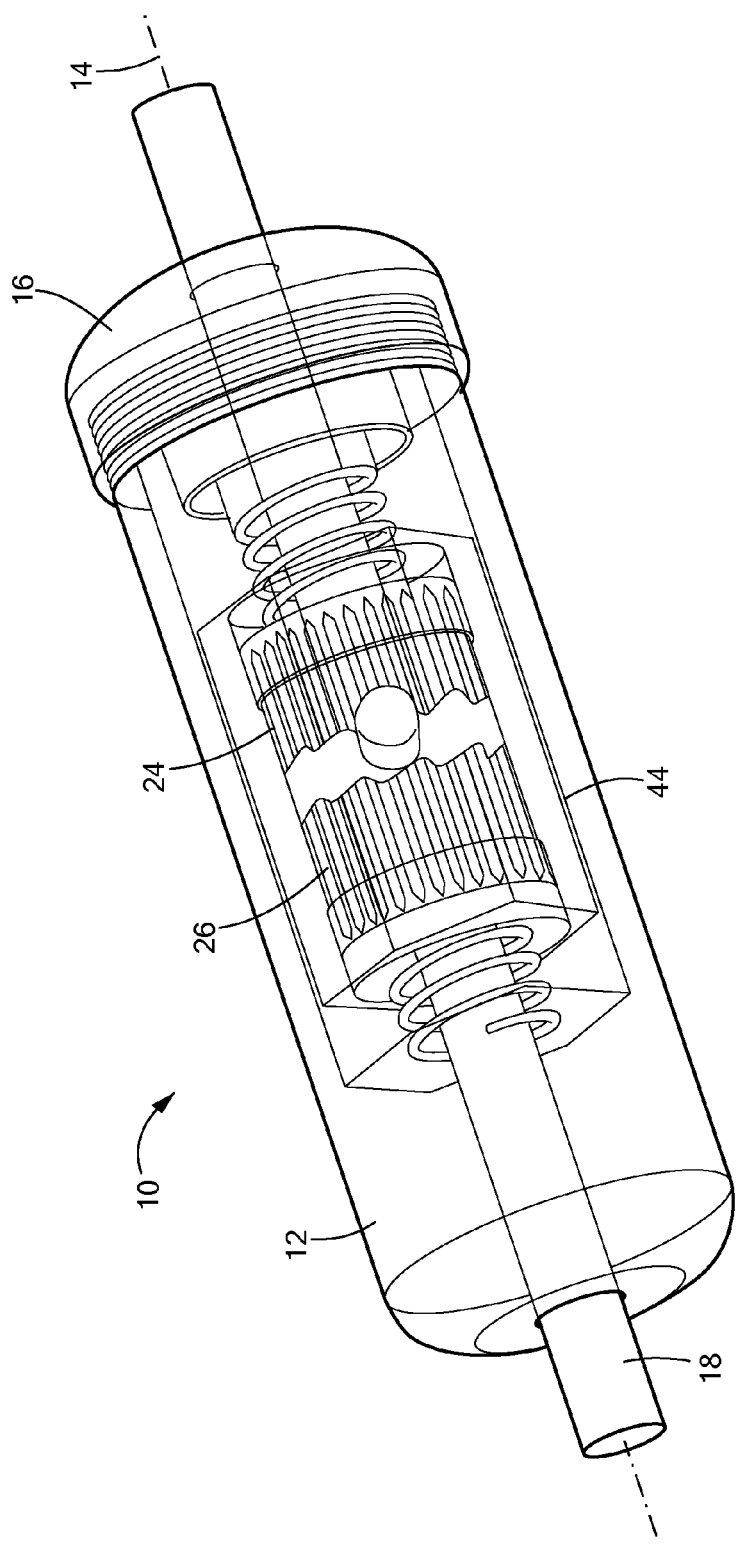
FIG. 1 is an illustration of an example of a torque-limited tool constructed in accordance with the principles of the present disclosure.
Figure 8:
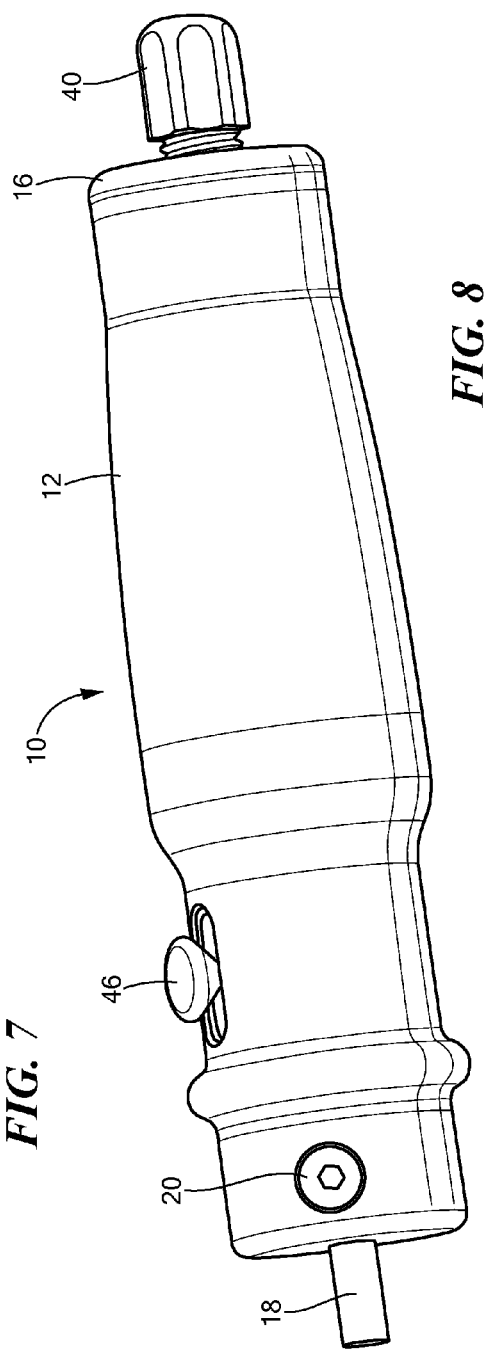
FIG. 8 is an illustration of another example of a torque-limited tool constructed in accordance with the principles of the present disclosure.

The tool 10 may generally include a graspable housing 12 or handle that contains or encloses components of a torque assembly, as describe herein. The handle may have a substantially cylindrical shape to facilitate ease of use (as shown in FIG. 1), and may include one or more augmented surfaces to enhance grip or ergonomics of using the tool 10 (as shown in FIG. 8). The handle may generally define a longitudinal axis 14 about which the handle rotates in order to rotate or drive a targeted fastener or piece of hardware. The handle or housing 12 may include a singular body defining one or more cavities or pockets therein to house components of the device, or the handle may include a plurality of components assembled together to facilitate the functions described herein.

The tool 10 may also include a cap 16 that is removably coupled to the handle to contain components therein. The cap 16 may include a washer, O-ring, or other pliable component to fluidically seal to the handle, thereby preventing unwanted debris or fluids from entering the inner workings of the tool 10.

Figure 9:
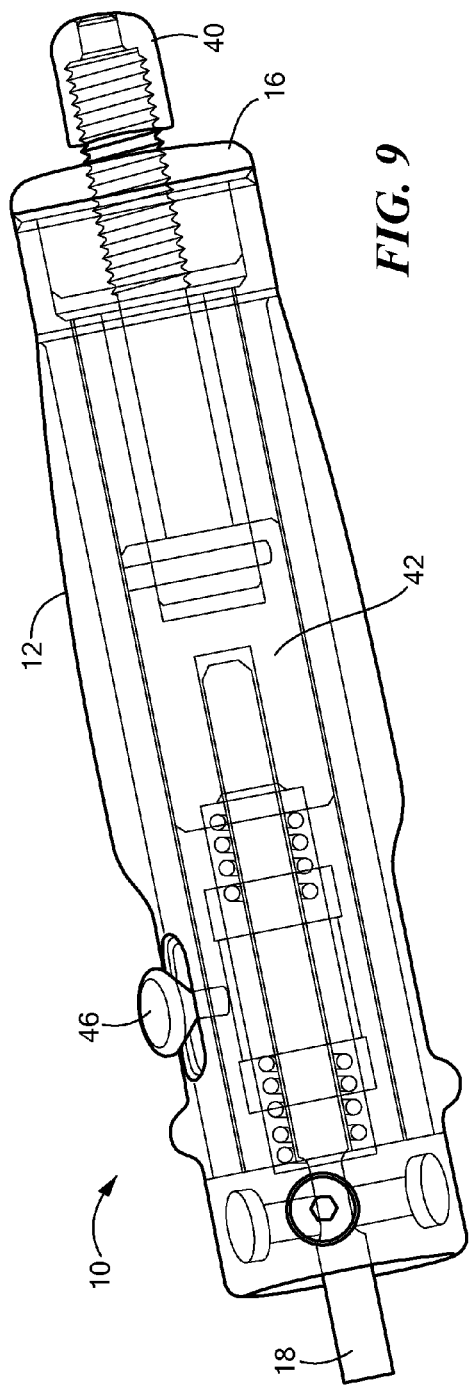
FIG. 9 is another illustration of the torque-limited tool of FIG. 8.
Figure 10:
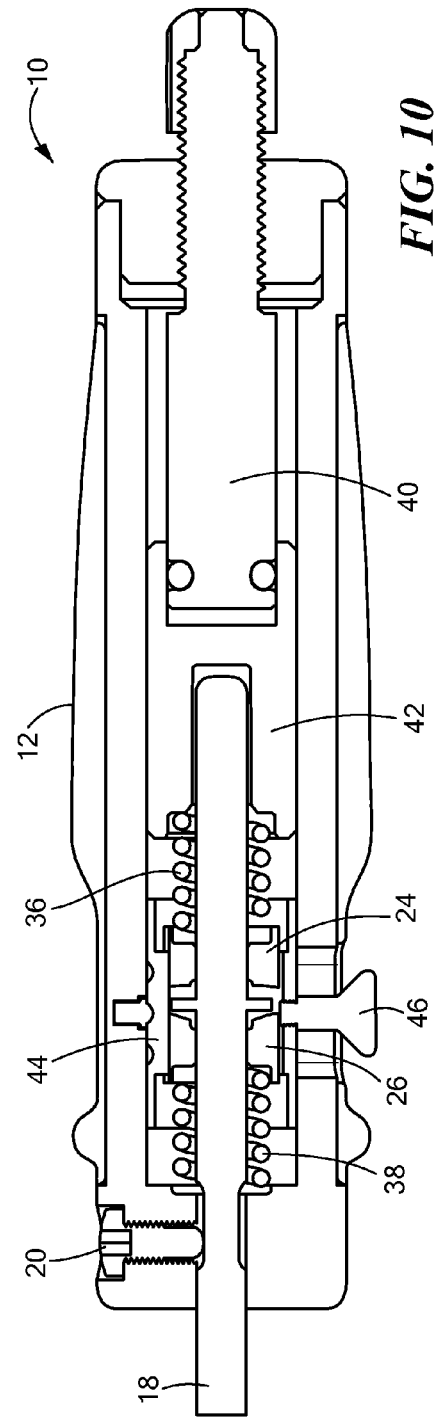
FIG. 10 is a cross-sectional view of the torque-limited tool of FIG. 8.

The tool 10 may include a shaft 18 coupled to and passing through at least a portion of the housing 12 that is engageable to a fastener or other surgical hardware (not shown) to drive, rotate, or otherwise interact with the hardware either directly or through one or more intermediate items, bits, or the like that can be coupled to an exposed end of the shaft 18. The shaft 18 may be coaxially disposed within the housing 12. As shown in FIGS. 8-10, a longitudinal position of the shaft 18 within a portion of the housing 12 may be adjustably secured by one or more locking elements 20 such as set screws or the like. A first gear 22 may be immovably coupled to the first shaft 18 within the handle. The first gear 22 may define a plurality of teeth on both an upward or proximal side of the first gear 22 (e.g., closer to a user) and a downward or distal side of the first gear 22 (e.g., closer to the hardware being driven or otherwise manipulated with the tool 10). The first gear 22 may be formed as a unitary construct with the first shaft 18 or may include a separate component that is secured to the shaft 18 through welding, an adhesive, or the like.

The tool 10 may include second and third gears 24, 26 disposed within the handle and coupled to the shaft 18, where a maximum torque transferable from the handle to the shaft 18 in a first rotational direction is limited at least in part by the second gear 24 and a maximum torque transferable from the handle to the shaft 18 in a second rotational direction is limited at least in part by the third gear 26. The second gear 24 may be coaxially disposed on the shaft 18 adjacent to the upper or proximal side of the first gear 22. The second gear 24 may be longitudinally movable on the shaft 18, and rotatable around the shaft 18. The third gear 26 may be coaxially disposed on the shaft 18 adjacent to the lower or distal side of the first gear 22. The third gear 26 may also be longitudinally movable and rotatable with respect to the shaft 18. Each of the second and third gears may define a plurality of teeth 28 engageable with the plurality of teeth on the respective sides of the first gear 22.

The teeth 28 of the second and third gears may be shaped, sloped, or otherwise angled to a predetermined degree to impart a maximum transferable torque threshold to the first gear 22 that, once exceeded, causes the second and/or third gears to step or slip with respect to the first gear 22 without turning the first gear 22. Now referring to FIGS. 5 and 11, for example, a least one tooth of the second gear 24 may define a first surface 30a that engages or presses against a surface of the first gear 22 in a first direction (e.g., clockwise) and a second surface 30b that engages or presses against a surface of the first gear 22 in a second direction (e.g., counter-clockwise). The first surface 30a of the tooth may be angled with respect to the longitudinal axis 14 to provide a desired degree of friction or force before the gear surfaces slide or step with respect to one another, thus limiting the torque transferable to the first gear 22 and the shaft 18. A reduction in the angle between the first surface 30a and the longitudinal axis 14 increases the force required to skip the gear interface, and thus, the greater the torque that can be applied to the first gear 22 and the shaft 18 (i.e., the closer to parallel the first surface is to the axis 14, the greater the transferable torque, and vice versa). An angle or slope of the second surface 30b may be less than the angle or slope of the first surface 30a such that less torque (or substantially zero torque) is applicable to the first gear 22 when the second gear 24 is turned in the second direction. This configuration allows the second gear 24 to be reversed without turning the first shaft 18 to enable a ratcheting operation of the tool 10.

The third gear 26 may include a similarly sloped or angled tooth configuration, but oppositely oriented to that of the second gear 24 such that torque is applicable through a first surface 32a of a tooth of the third gear 26 in the second direction, with minimal or substantially zero torque applied through a second surface 32b of a tooth of the third gear 26 when turned in the first direction.

Figure 5:
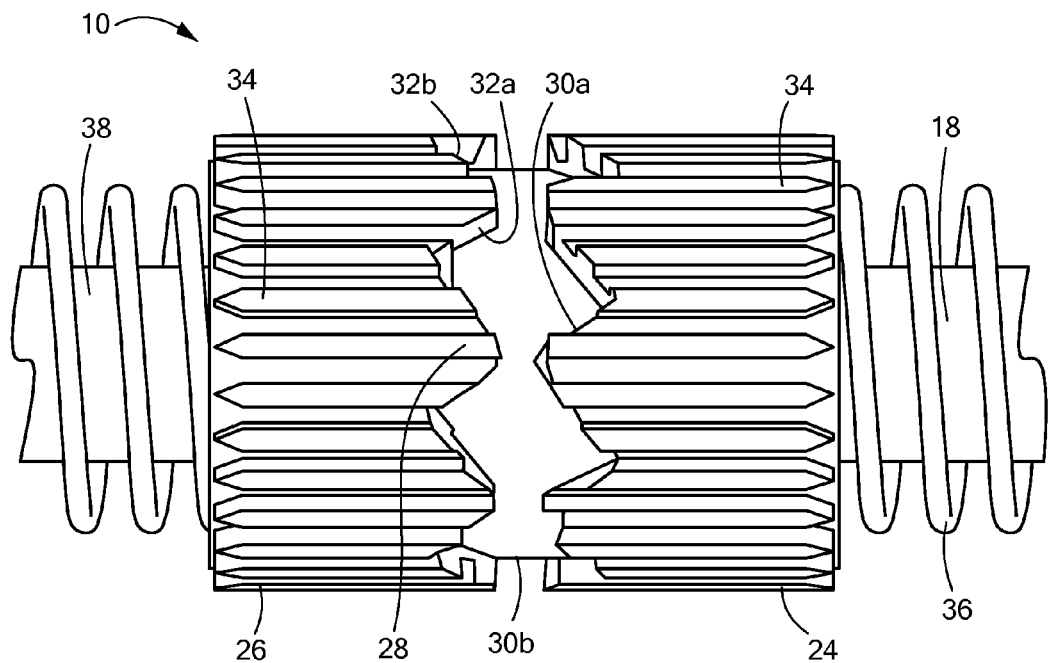
FIG. 5 is another illustration of an example of a gearing assembly of the torque-limited tool of FIG. 1.
Figure 6:
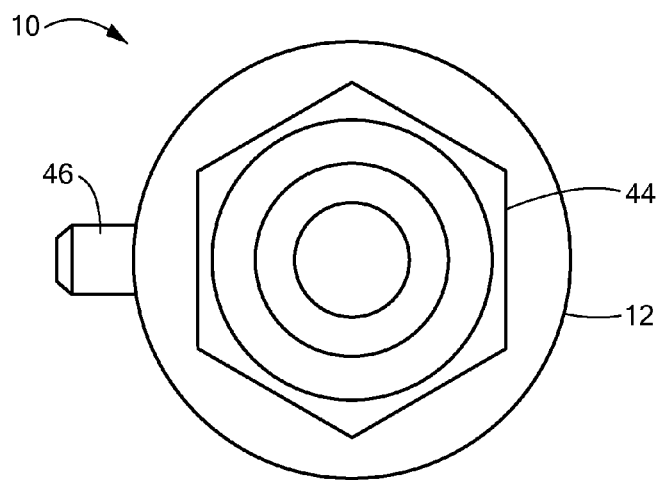
FIG. 6 is an illustration of an end view of the torque-limited tool of FIG. 1.
Figure 11:
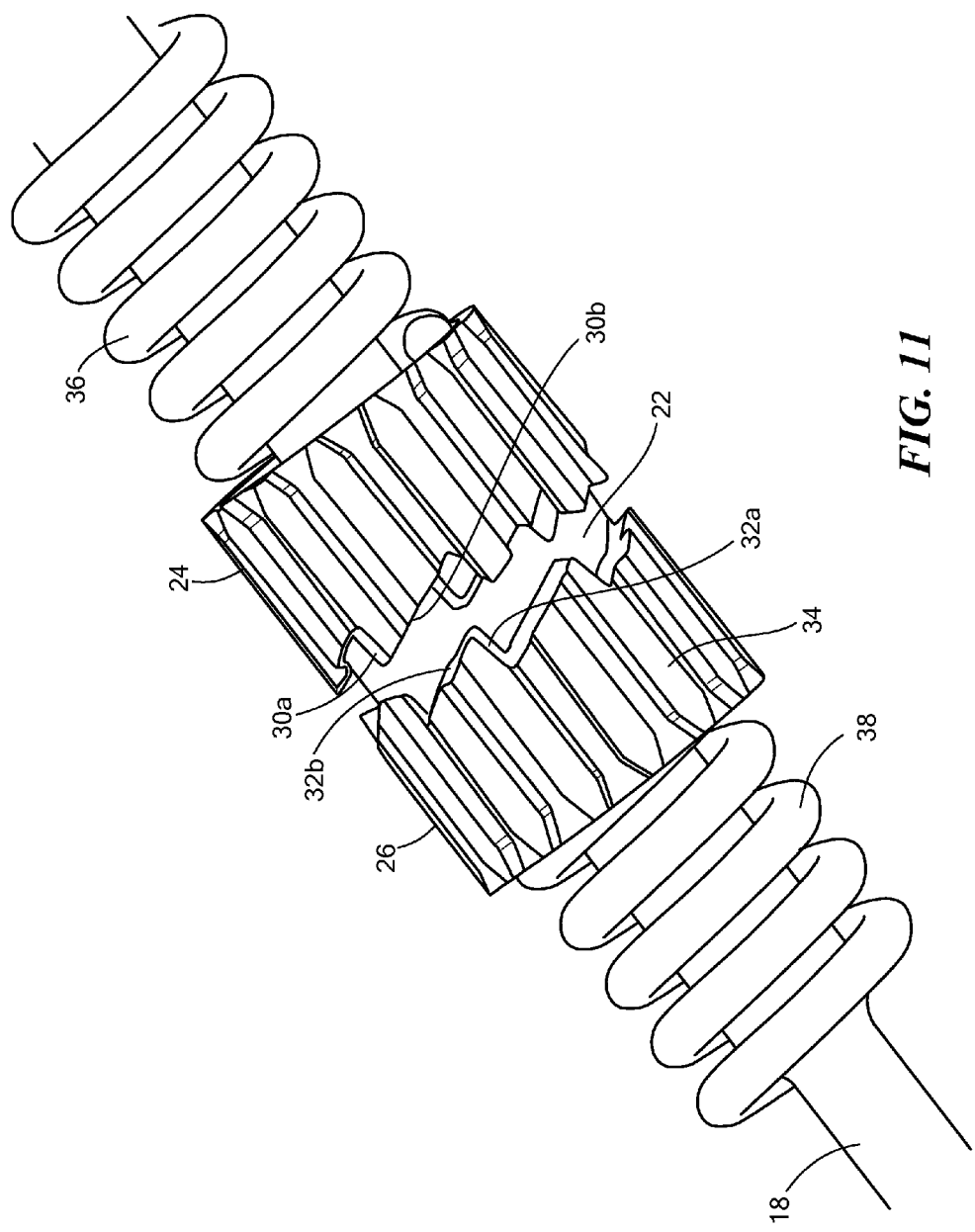
FIG. 11 is an illustration of an example of a gearing assembly of the torque-limited tool of FIG. 8.

Now referring to FIGS. 5 and 11, the second and third gears 24, 26 may each include or define a plurality of splines 34 on their exterior surfaces. The longitudinally-oriented splines may be spaced apart around all or a portion of the circumference of each respective gear, thereby defining a space or depressed surface therebetween.

The tool 10 may include one or more resistive or resilient elements or components to resist longitudinal movement of the second and/or third gears, and accordingly, the force required to skip or step either of the second and third gears with respect to the first gear 22. For example, the tool 10 may include a first spring 36 disposed between the handle and the second gear 24 to resist movement or displacement of the second gear 24 in a proximal or upward direction. The tool 10 may also include a second spring 38 disposed between the third gear 26 and the handle to resist movement or displacement of the third gear 26 in a distal or downward direction.

Figure 2:
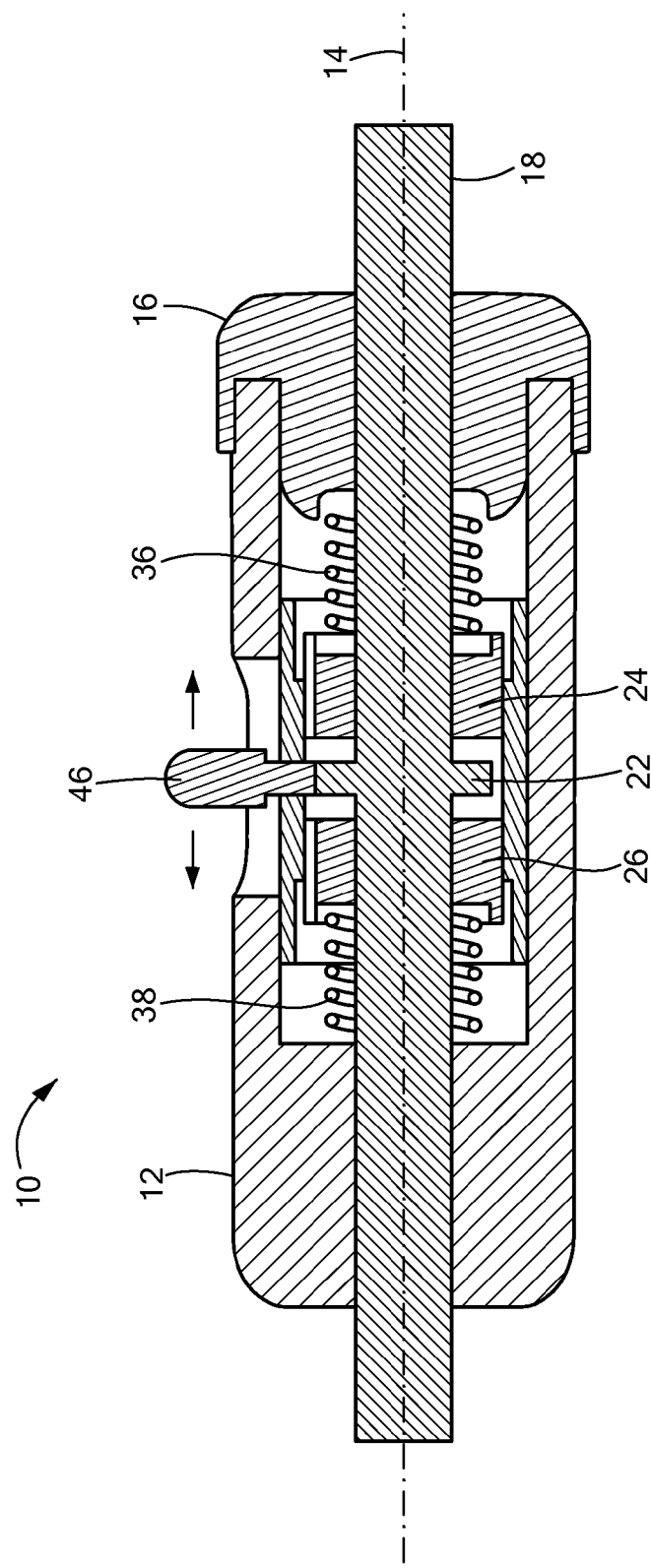
FIG. 2 is a cross-sectional view of the torque-limited tool of FIG. 1.
Figure 3:
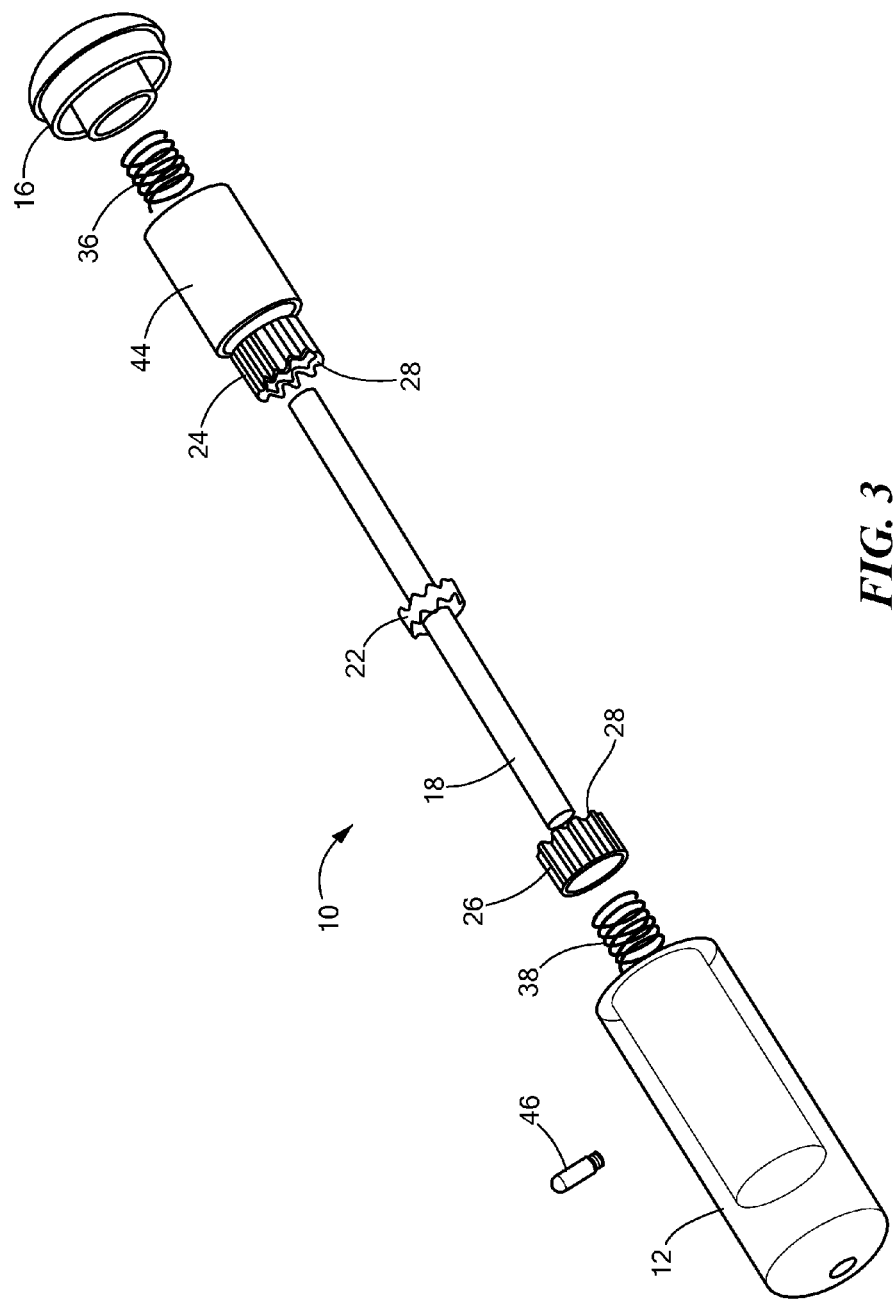
FIG. 3 is an exploded assembly illustration of the torque-limited tool of FIG. 1.

The resistance or resiliency of the springs may be predetermined and/or adjustable to facilitate selection of a maximum transferable torque to the first gear 22 and the shaft 18. For example, as shown in FIGS. 1-2, the first and/or second springs may be coupled to the cap 16 such that manipulation of the cap 16 imparts increased or decrease pre-compression onto the spring(s). The cap 16 may rotatable to increase the stiffness or resistance of the first or second springs, and/or may be axially or longitudinally depressible to manipulate the experienced compression of the springs, thereby adjusting the resultant force needed to displace or step the second or third gear 26 with respect to the first gear 22. Alternatively, as shown in FIGS. 8-10, the first or second springs may be adjusted by an adjustment actuator 40 at least partially disposed in the housing 12 and coupled to the cap 16 and the springs. The adjustment actuator 40 may include a threaded portion that engages threads on an interior passage through the cap 16, such that turning the adjustment actuator 40 results in its longitudinal displacement within a portion of the housing 12, resulting in the compression or expansion of the first and/or second springs. The adjustment actuator 40 may couple to the springs directly, or alternatively, the tool 10 may include a shuttle 42 movably disposed in the housing 12 and coupled to the adjustment actuator 40 at one end, while being connected to the first or second spring at a second end. Movement of the adjustment actuator 40 results in movement of the shuttle 42, and thus the compression or expansion of the springs.

Figure 4:
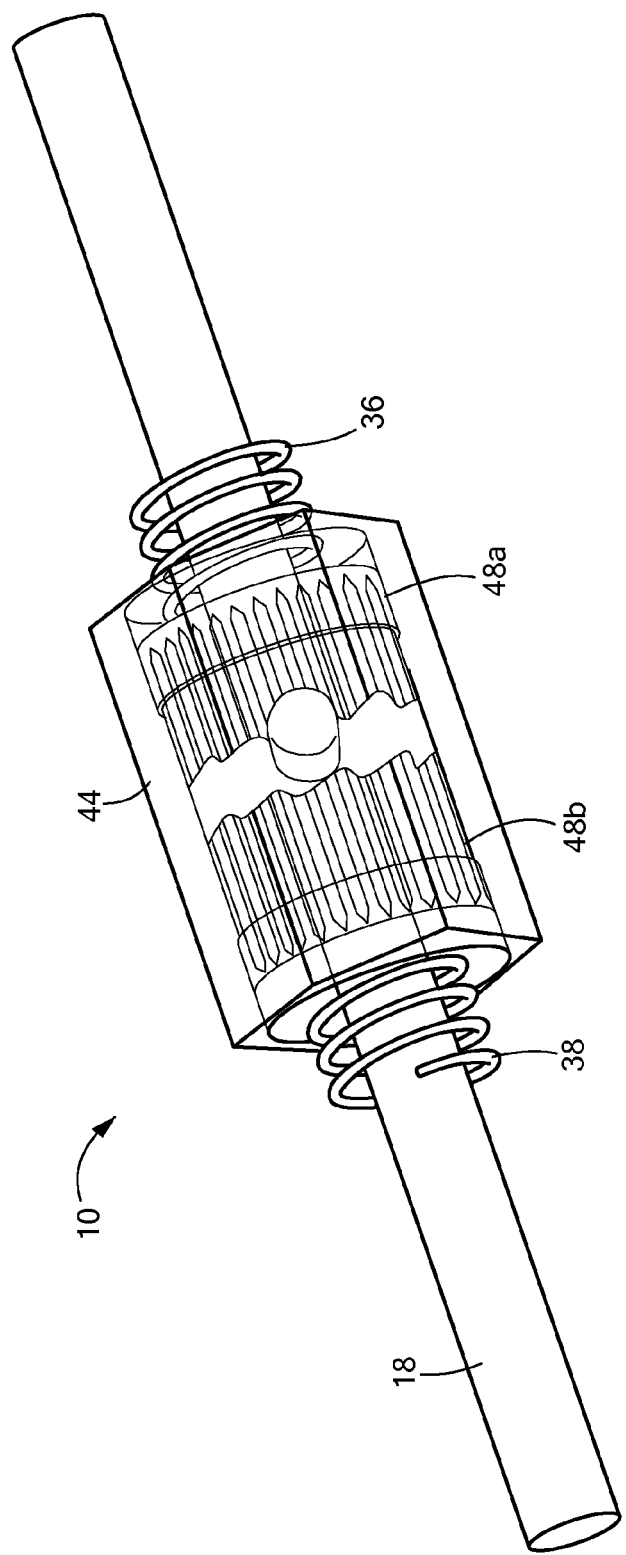
FIG. 4 is an illustration of an example of a gearing assembly of the torque-limited tool of FIG. 1.
Figure 7:
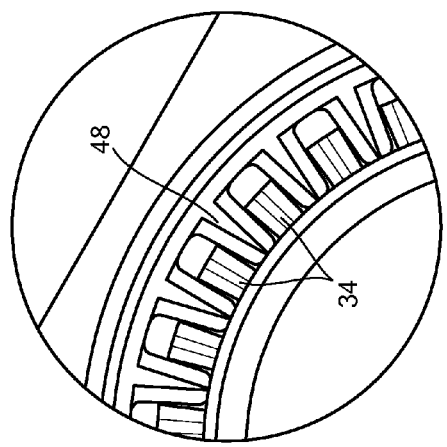
FIG. 7 is a detail illustration of a portion of the torque-limited tool end view of FIG. 6.
Figure 12:
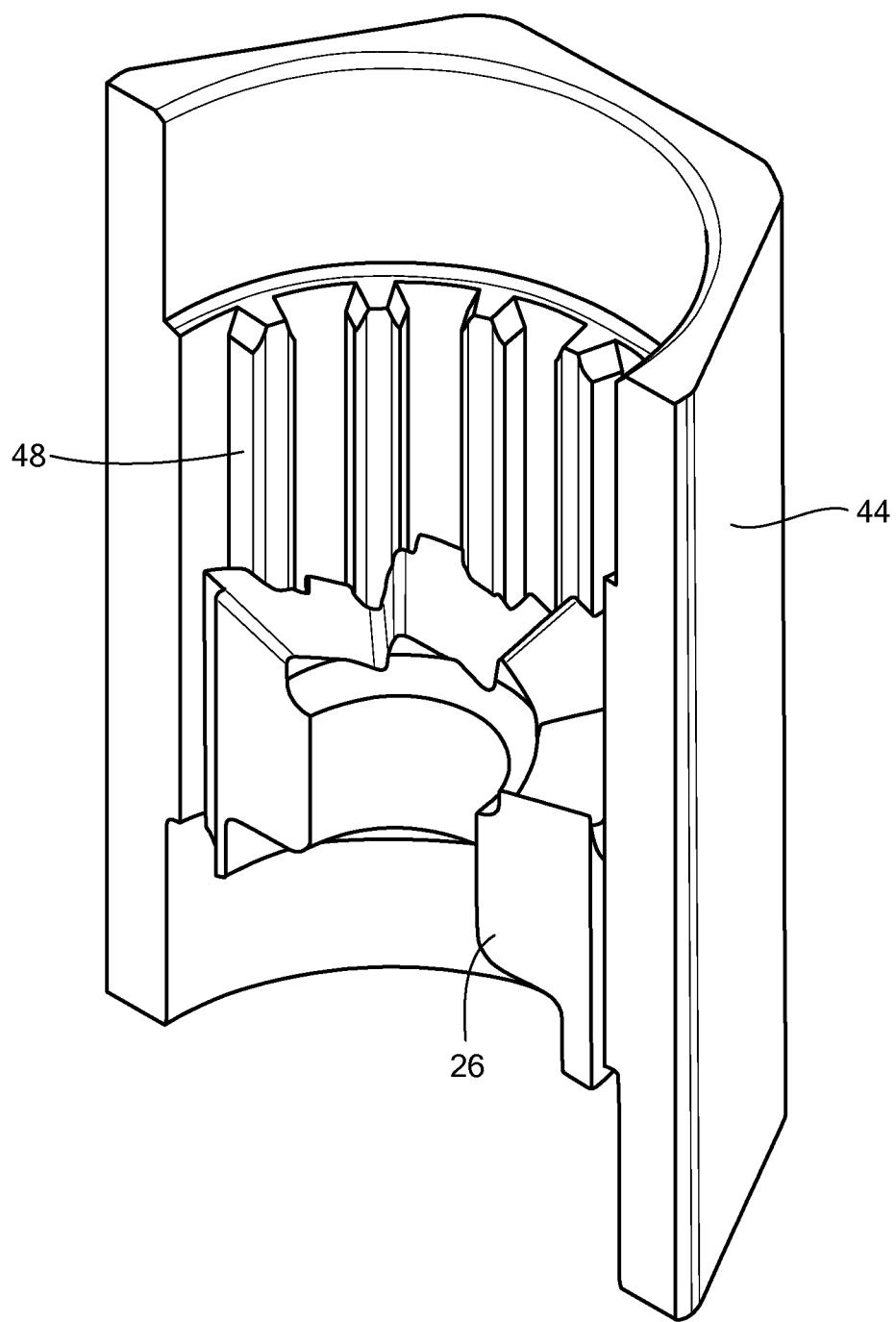
FIG. 12 is another illustration of an example of a gearing assembly of the torque-limited tool of FIG. 8.

The tool 10 may further include a selector element or mechanism operable to selectively engage the handle to one of the first gear 22, second gear 24, and/or third gear 26 depending on the direction of rotation the tool 10 is being used in and whether ratcheting is desired. For example, as shown in FIGS. 4 and 12, a sleeve 44 may be disposed within and movably coupled to the housing 12. The sleeve 44 may be movable into three discrete positions, each of which fixedly couples the handle to the first gear 22, second gear 24, and/or third gear 26. The tool 10 may include a selector pin, knob, or lever 46 accessible from an exterior of the tool 10 and coupled to the sleeve 44 to aid in moving the sleeve 44 into a desired position. The sleeve 44 may define a plurality of longitudinally-oriented rails 48 that are slidably movable in between the splines 34 of the respective gear(s) to fix the rotational alignment and coupling between the sleeve 44 (and thus the handle) and the particular engaged gear(s), while the longitudinal orientation of the splines 34 allows the second or third gear 26 to still displace or skip with respect to the first gear 22 when the torque threshold is surpassed. An illustration of the engaged splines and rails is shown in FIG. 7.

In the example shown in FIG. 4, two different sets of rails 48a, 48b are spaced apart and located on opposite ends of the sleeve 44. The rails 48a at an upper end of the sleeve 44 engage the second gear 24 when the sleeve 44 is moved downward, which also results in rails 48b at the bottom of the sleeve 44 disengaging the third gear 26. In the example shown in FIGS. 10 and 12, the rails 48 are substantially continuous and centrally located on an interior of the sleeve 44. In this example, the sleeve 44 is moved upward to engage the rails 48 of the second gear 24, which also disengages the rails from the third gear 26. When the sleeve 44 engages the handle to the second gear 24 (for example, when the rails of the sleeve 44 are engaged with the splines of the second gear 24), the transferable torque is limited in the first rotational direction, and provides reduced or substantially zero torque transfer between the handle and the first gear 22 in the second direction, allowing a user to ratchet the tool 10 in the second direction without affecting movement or position of the shaft 18.

Oppositely, when the sleeve engages the handle or housing 12 to the third gear 26 (such as when the rails 48 of the sleeve 44 are engaged with the splines of the third gear 26), the transferable torque is limited in the second rotational direction, and provides reduced or substantially zero torque transfer between the handle and the first gear 22 in the first direction, allowing a user to ratchet the tool 10 in the first direction without affecting movement or position of the shaft 18. This selectable position can be achieved, for example, by moving the sleeve 44 upward in the example shown in FIG. 4, while moving the sleeve 44 downward will accomplish the engagement to the third gear 26 for the example in FIGS. 10 and 12.

The sleeve 44 may also be positioned to engage both the second and third gears at the same time, thus providing torque-limited turning in both the first and second directions. The sleeve 44 may be placed into an intermediary position such that the rails 48 engage at least a portion of the splines 34 of both the second and third gears to effect the bi-directional torque-limited operation.

It will be appreciated by persons skilled in the art that the present invention is not limited to what has been particularly shown and described herein above. In addition, unless mention was made above to the contrary, it should be noted that all of the accompanying drawings are not to scale. Of note, the system components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein. Moreover, while certain embodiments or figures described herein may illustrate features not expressly indicated on other figures or embodiments, it is understood that the features and components of the examples disclosed herein are not necessarily exclusive of each other and may be included in a variety of different combinations or configurations without departing from the scope and spirit of the invention. A variety of modifications and variations are possible in light of the above teachings without departing from the scope and spirit of the invention, which is limited only by the following claims.

What is claimed is:

1. A tool having limited torque transference, comprising:
   a shaft;
   a first gear fixed to the shaft;
   a first tooth engageable with the first gear and rotatable with respect to the shaft; and
   a second tooth engageable with the first gear and rotatable with respect to the shaft, wherein a maximum torque threshold applied to the shaft in a first rotational direction is limited at least in part by a slope of the first tooth and a maximum torque threshold applied to the shaft in a second rotational direction is limited at least in part by a slope of the second tooth.

2. The tool of claim 1, wherein at least one of the first or second teeth are longitudinally movable with respect to the shaft.

3. The tool of claim 2, further comprising a spring that resists the longitudinal movement of the at least one of the first or second teeth.

4. The tool of claim 3, wherein the resistance of the spring is selectively adjustable.

5. The tool of claim 1, further comprising a housing and a handle co-axial with the shaft, wherein the shaft, first gear, first tooth, and second tooth are contained within the handle.

6. The tool of claim 5, wherein the housing is selectively engageable to the first tooth or the second tooth.

7. The tool of claim 5, wherein the housing is selectively engageable to the first gear.

8. A ratchet tool, comprising:
a housing;
a shaft passing through at least a portion of the housing and defining a longitudinal axis;
a first gear immovably fixed to the shaft;
a second gear disposed in the housing and rotatable with respect to the shaft; and
a third gear disposed in the housing and rotatable with respect to the shaft, wherein a maximum torque transferable from the housing to the shaft in a first rotational direction is limited at least in part by the second gear and a maximum torque transferable from the housing to the shaft in a second rotational direction is limited at least in part by the third gear.

9. The ratchet tool of claim 8, wherein the second and third gears are coaxial with the shaft.

10. The ratchet tool of claim 9, wherein the housing is selectively engageable with the first gear, second gear, or third gear.

11. The ratchet tool of claim 10, further comprising a selector pin movably coupled to the housing, wherein the selector pin is positionable in a plurality of positions to selectively engage the housing with the second gear or third gear.

12. The ratchet tool of claim 11, further comprising a sleeve coupled to the selector pin, the sleeve defining a plurality of rails engageable with a plurality of longitudinal splines defined by the second gear or third gear.

13. The ratchet tool of claim 8, further comprising:
a first spring disposed between the second gear and the housing; and
a second spring disposed between the third gear and the housing.

14. The ratchet tool of claim 8, wherein a compression of at least one of the first or second springs is selectively adjustable.

15. The ratchet tool of claim 14, further comprising a cap coupled to the housing, wherein the cap is operable to adjust the compression of the first or second springs.

16. The ratchet tool of claim 8, wherein the second gear defines at least one tooth engageable with the first gear, the tooth defining a first surface defining a first angle with respect to the longitudinal axis and a second surface defining a second angle with respect to the longitudinal axis, wherein the first angle is smaller than the second angle.

17. The ratchet tool of claim 16, wherein the third gear defines at least one tooth engageable with the first gear, the tooth defining a first surface defining a first angle with respect to the longitudinal axis and a second surface defining a second angle with respect to the longitudinal axis, wherein the first angle is smaller than the second angle.

18. A ratchet tool, comprising:
a shaft defining a longitudinal axis;
a handle coaxial to the shaft;
a first gear immovably fixed to the shaft and disposed in the handle;
a second gear rotatably and longitudinally movable with respect to the shaft, wherein the second gear engages the first gear to limit torque transfer from the handle to the shaft in a first direction and provides substantially zero torque transfer in a second direction;
a first spring disposed between the second gear and the handle;
a third gear rotatably and longitudinally movable with respect to the shaft, wherein the third gear engages the first gear to limit torque transfer from the handle to the shaft in the second direction and provides substantially zero torque transfer in the first direction; and
a second spring disposed between the third gear and the handle.

19. The ratchet tool of claim 18, further comprising a cap coupled to the handle, wherein the cap is operable to adjust a compression of at least one of the first or second springs.

20. The ratchet tool of claim 18, further comprising a selector element movably coupled to the handle to selectively engage the handle to one of the first gear, second gear, or third gear.

* * * * *